(12) United States Patent
Sakaguchi et al.

(10) Patent No.: US 9,561,140 B2
(45) Date of Patent: Feb. 7, 2017

(54) DISPOSABLE DIAPER

(71) Applicant: UNICHARM CORPORATION, Shikokuchuo-shi, Ehime (JP)

(72) Inventors: Satoru Sakaguchi, Kanonji (JP); Kana Sawa, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 0 days.

(21) Appl. No.: 14/375,590

(22) PCT Filed: Feb. 1, 2013

(86) PCT No.: PCT/JP2013/052315
§ 371 (c)(1),
(2) Date: Jul. 30, 2014

(87) PCT Pub. No.: WO2013/115346
PCT Pub. Date: Aug. 8, 2013

(65) Prior Publication Data
US 2015/0025491 A1    Jan. 22, 2015

(30) Foreign Application Priority Data
Feb. 1, 2012   (JP) .................. 2012-020378

(51) Int. Cl.
*A61F 13/15*    (2006.01)
*A61F 13/56*    (2006.01)
(Continued)

(52) U.S. Cl.
CPC ..... *A61F 13/5633* (2013.01); *A61F 13/51476* (2013.01); *A61F 13/51496* (2013.01);
(Continued)

(58) Field of Classification Search
CPC .................. A61F 13/51496; A61F 2013/8497
(Continued)

(56) References Cited

U.S. PATENT DOCUMENTS 6,210,389 B1   4/2001   Long et al.
2003/0045854 A1*   3/2003   Yoshioka ............ A61F 13/5622
                                                    604/386

(Continued)

FOREIGN PATENT DOCUMENTS

JP    2002-017778 A    1/2002
JP    2003-70840 A    3/2003
(Continued)

OTHER PUBLICATIONS

International Search Report in International Application No. PCT/JP2013/052315 mailed Mar. 5, 2013 with English language translation.
(Continued)

*Primary Examiner* — Bradley Philips
(74) *Attorney, Agent, or Firm* — Hauptman Ham, LLP (57) ABSTRACT

The disposable diaper according to the present invention includes a base sheet (12) made of nonwoven fabric and a hook sheet (110) provided with a plurality of engagement hooks. A KES bending stiffness value in a fastening tape existent region (SHS) is equal to or less than 1.64 gf·cm²/cm, the height of the engagement hook is between 60 and 200 μm; and the color difference (ΔE) between the hook sheet existent region (SHS) on the inner side of a fastening tape (100) and side flaps (50) adjacent to the fastening tape (100) is 6.5 or more, when the color difference of L* is ΔL*, the color difference of a* is Δa*, and the color difference of b* is Δb* according to the L*a*b* color coordinate system.

10 Claims, 4 Drawing Sheets

(51) Int. Cl.
*A61F 13/514* (2006.01)
*A61F 13/62* (2006.01)
*A61F 13/84* (2006.01)

(52) U.S. Cl.
CPC .......... *A61F 13/625* (2013.01); *A61F 13/627* (2013.01); *A61F 2013/15357* (2013.01); *A61F 2013/8497* (2013.01)

(58) Field of Classification Search
USPC .......................................................... 604/391
See application file for complete search history.

(56) References Cited

U.S. PATENT DOCUMENTS

| | | | | |
|---|---|---|---|---|
| 2004/0153046 A1* | 8/2004 | Ito | ........................... | A61F 13/62 604/391 |
| 2005/0080394 A1* | 4/2005 | Otsubo | ............. | A61F 13/49011 604/385.27 |
| 2008/0021431 A1* | 1/2008 | Kenmochi | ............ | A61F 13/565 604/385.23 |
| 2008/0132872 A1* | 6/2008 | Trennepohl | ....... | A61F 13/15699 604/385.24 |
| 2011/0015608 A1* | 1/2011 | Fujioka | ............. | A61F 13/15731 604/389 |

FOREIGN PATENT DOCUMENTS

| | | |
|---|---|---|
| JP | 2004-167025 A | 6/2004 |
| JP | 2005-40231 A | 2/2005 |
| JP | 2011-67602 A | 4/2011 |

OTHER PUBLICATIONS

Office Action in EA Patent Application No. 201400814, mailed Apr. 4, 2016.
Office Action mailed Oct. 27, 2015, corresponding to Japanese Patent Application No. 2012-020378.
Office Action dated Sep. 18, 2015, corresponding to Chinese Patent Application No. 201380007797.1.

* cited by examiner

DISPOSABLE DIAPER

RELATED APPLICATIONS

The present application is a National Phase of International Application Number PCT/JP2013/052315, filed Feb. 1, 2013, which claims priority to Japanese Patent Application No. 2012-020378, filed Feb. 1, 2012.

TECHNICAL FIELD

The present invention relates to a disposable diaper provided with a fastening tape at one of a front waistline portion and a back waistline portion thereof.

BACKGROUND ART

In the conventional art, as a disposable diaper mainly used in an infant and toddler and the like, there is widely provided so called an open-type disposable diaper provided with a fastening tape for fixing at side flaps of a back waistline portion (or a front waistline portion) thereof. The open-type disposable diaper provided with the above-described fastening tape has been widely used, in particular, in a new-born baby and an infant and toddler because it is easily attachable and detachable.

In the above open-type disposable diaper, there has been known a structure in which a proximal end of a skin contact surface side of the fastening tape is covered by side flaps (nonwoven fabric) more flexible than the fastening tape (for example, Patent Literature 1). According to the above disposable diaper, since the fastening tape prevents the skin of an infant and toddler and the like from being stimulated, it is difficult for the infant and toddler to feel discomfort or pain.

CITATION LIST

Patent Literature

[PTL 1]
Japanese Unexamined Patent Application Publication No. 2003-70840 (FIG. 1)

SUMMARY OF INVENTION

Meanwhile, in recent years, demands of a user (a purchaser) for a disposal diaper are increased, and specifically, when an infant wears the disposal diaper, there is an increased awareness that the user would like to cause no burden to the skin of the infant or reduce a burden to the skin of the infant if possible.

However, even when the above-described conventional fastening tape is applied, there is a concern that the fastening tape causes great uncomfortable feeling specifically in texture or appearance, as compared with other portions of a disposable diaper made of nonwoven fabric and the like, and that is may not be completely possible to dispel the anxiety shared by the recent-year user who has increased demands for the disposable diaper.

On the other hand, because the fastening tape has the function of retaining the disposable diaper on to the body, if the portion that retains the disposable diaper on to the body, specifically, the portion (hook portion) with which the fastening tape provided in the back body (or front body) can be engaged with the front body (or back body) cannot be identified, the impression that the fastening tape does not offer the uncomfortable feeling, and at the same time, the problem of the fear of insecurity that the fastening tape might easily come off and the disposable diaper might fall off the body is seen.

Therefore, the present invention has been achieved in view of the above-described situation, and an object thereof is to provide a disposable diaper that can offer an impression of having a sufficient engagement strength while significantly reducing the uncomfortable feeling in texture or appearance of a fastening tape.

A characteristic of the present invention is summarized as a disposable diaper having a longitudinally elongated absorbent main body (absorbent main body 15) configured by a front waistline portion (front waistline portion 20), a back waistline portion (back waistline portion 40), and a crotch portion (crotch portion 30) and including a liquid-retentive absorber (absorber 35); side flaps (side flaps 50) provided in at least a part of the side edges in the widthwise direction of the absorbent main body; and a fastening tape (fastening tape 100) attached to the side flaps and extending outside in the widthwise direction of the absorbent main body from one of the front waistline portion and the back waistline portion, and configured to be fixedly worn to a remaining one of the front waistline portion and the back waistline portion, such that the fastening tape has a base sheet (base sheet 120) and a hook sheet (hook sheet 110) provided with a plurality of engagement hooks, and in the fastening tape existent region (fastening tape existent region SALL) provided with the fastening tape, the KES bending stiffness value per unit length in the longitudinal direction of the absorbent main body of the hook sheet existent region (hook sheet existent region SHS) provided with the hook sheet, and the KES bending stiffness value per unit length in the widthwise direction of the absorbent main body is equal to or less than 1.64 gf·cm$^2$/cm, the height of the engagement hook is between 60 and 200 µm, and the color difference ΔE between the hook sheet existent region on the inner side of the fastening tape and the side flaps adjacent to the fastening tape is 6.5 or more when the color difference of L* is ΔL*, the color difference of a* is Δa*, and the color difference of b* is Δb* according to the L*a*b* color coordinate system.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

(1) SCHEMATIC SHAPE OF DISPOSABLE DIAPER

Figure 1:
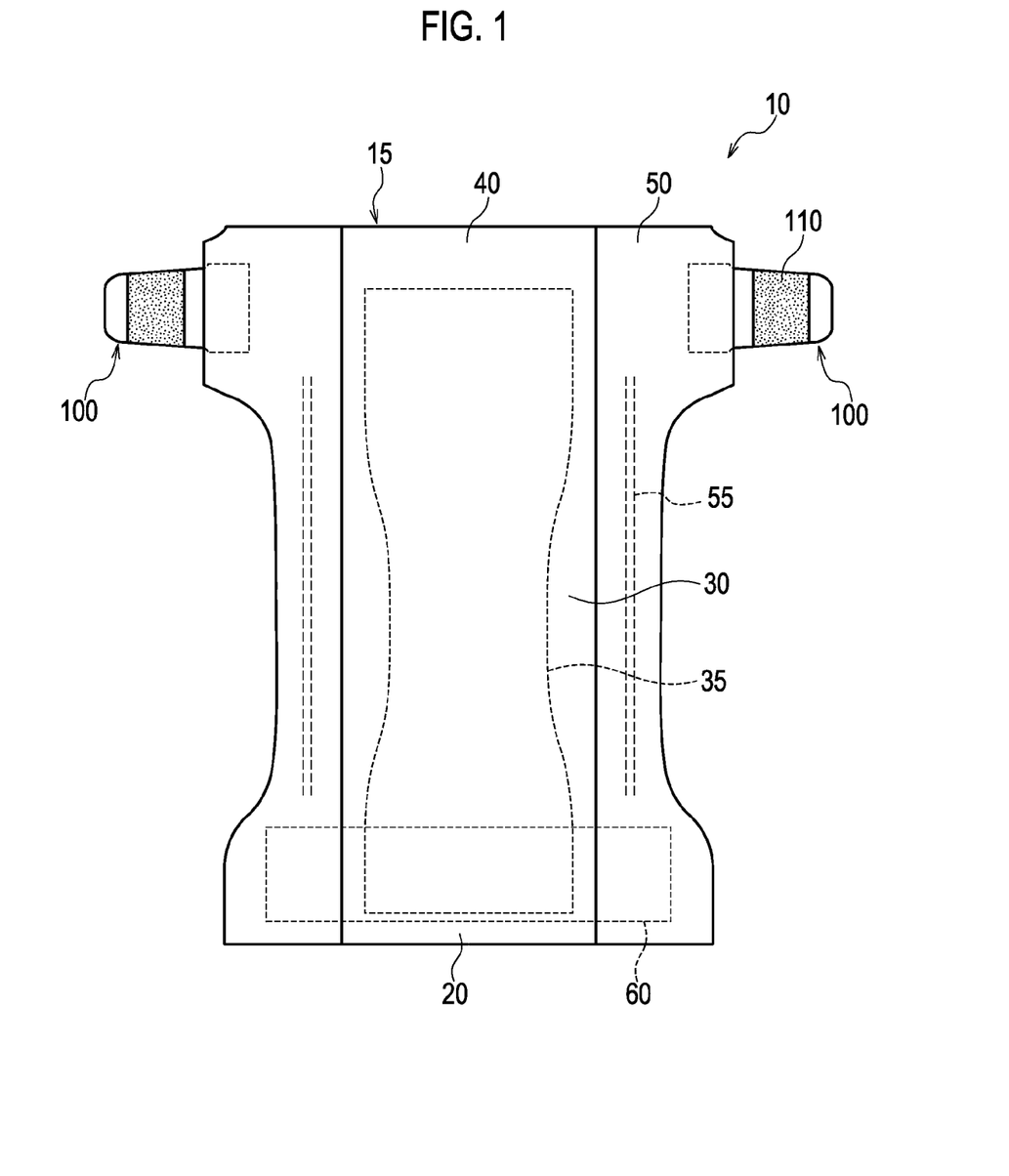
FIG. 1 is a plan view of a disposable diaper 10 according to an embodiment of the present invention.

FIG. 1 is a plan view of a disposable diaper 10 according to the present embodiment. As shown in FIG. 1, the disposable diaper 10 is an open-type diaper having a front waistline portion 20, a crotch portion 30, and a back waistline portion 40. The disposable diaper 10 can be used favorably for infants and toddlers in particular.

An absorbent main body 15 is configured by the front waistline portion 20, the crotch portion 30, and the back waistline portion 40. The absorbent main body 15 has a longitudinally elongated shape including an absorber 35 with liquid retention property. In the present embodiment, the absorber 35 is provided across the front waistline portion 20, the crotch portion 30, and the back waistline portion 40. The absorber 35 has a shape such that the width of the absorber 35 in the central portion in the longitudinal direction DL of the absorbent main body 15 is narrow. The shape of the absorber 35 is not limited to the shape shown in FIG. 1, and may also be a simple rectangle. Furthermore, the absorber 35 must at least be provided in the crotch portion 30.

The absorbent main body 15 is similar to the conventional open-type disposable diaper, and can be configured appropriately by using well-known members and material. Furthermore, the absorbent main body 15 may also include a liquid-permeable topsheet, solid gathers provided in the side edges of the absorbent main body 15 along the longitudinal direction DL, and waist gathers provided in the back waistline portion 40 along the widthwise direction DW, which are not shown in the figure.

Side flaps 50 are provided in the side edges in the widthwise direction DW of the absorbent main body 15. The side flaps 50 are configured by one layer of nonwoven fabric or two or more plurality of layers of nonwoven fabric layered on each other.

In the present embodiment, the side flaps 50 are provided across the entire region in the longitudinal direction DL of the absorbent main body 15. That is, the side flaps 50 are provided from the front waistline portion 20 up to the back waistline portion 40. The width of the side flaps 50 corresponding to the crotch portion 30 is lesser than the width of the side flaps 50 corresponding to the front waistline portion 20 and the back waistline portion 40. It must be noted that the side flaps 50 need not necessarily be provided across the entire region in the longitudinal direction DL of the absorbent main body 15, for example, the side flaps 50 may be provided only in the region corresponding to the back waistline portion 40.

Furthermore, in the side edges in the widthwise direction DW of the absorbent main body 15, specifically, in the side flaps 50, stretchable leg elastic members 55 are provided along the longitudinal direction DL of the absorbent main body 15. The absorbent main body 15 is contracted in the longitudinal direction DL by the leg elastic members 55. The absorbent main body 15 thus contracted can be, particularly, stretched in the longitudinal direction DL at the back waistline portion 40 side.

The fastening tape 100 is installed in the side flaps 50. Specifically, the fastening tape 100 extends towards the outer side in the widthwise direction DW of the absorbent main body 15 from the back waistline portion 40. The fastening tape 100 is configured to be fastened to the front waistline portion 20. A hook sheet 110 (not shown in FIG. 1; see FIG. 2) of the fastening tape 100 is configured to engage with a target tape 60 provided at the back sheet 70 (not shown in FIG. 1; see FIG. 3) side of the front waistline portion 20.

The fastening tape 100 may be installed in the side flaps 50 to extend towards the outer side in the widthwise direction DW of the absorbent main body 15 from the front waistline portion 20, rather than the back waistline portion 40, and in the case of infants and toddlers for whom the disposable diaper is changed mostly while lying face upward, the fastening tape 100 is desired to be installed in the back waistline portion 40.

(2) SHAPE OF FASTENING TAPE

Figure 2:
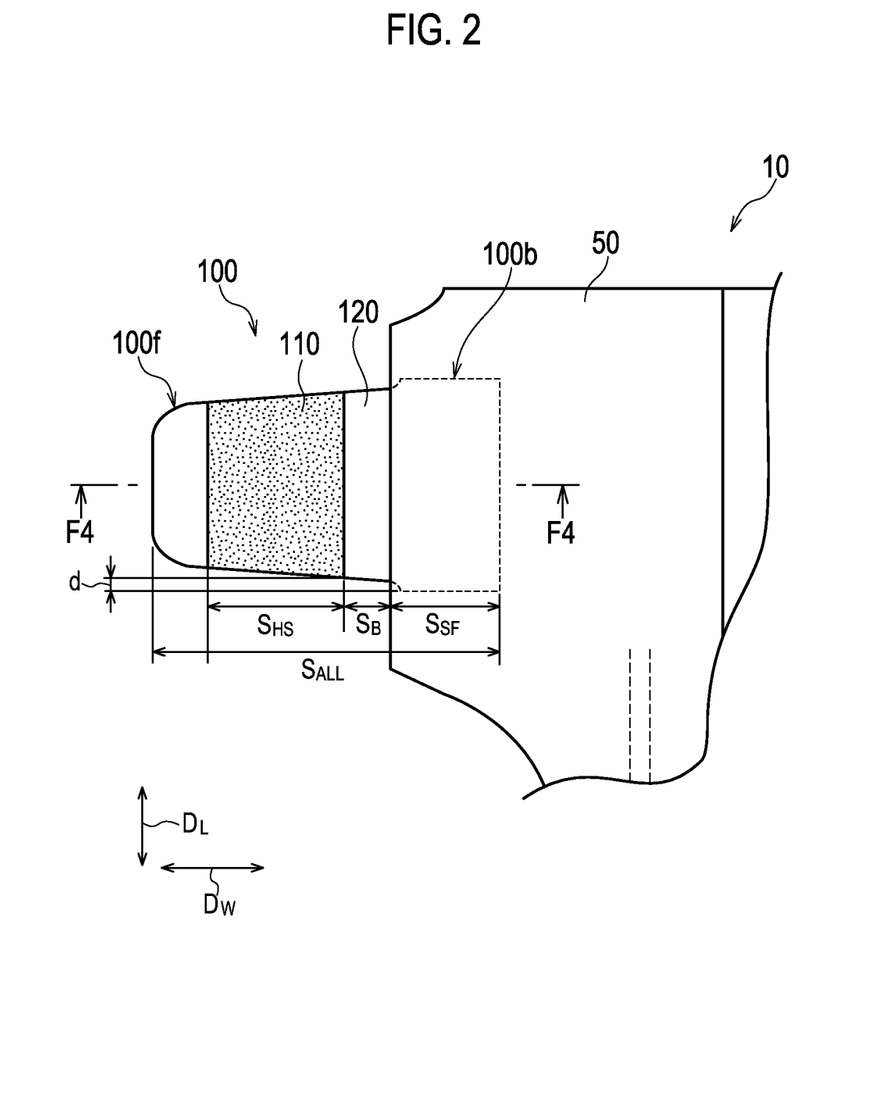
FIG. 2 is an enlarged view of a fastening tape 100 portion (a side of a side flap 50) of the disposable diaper 10 according to the embodiment of the present invention.
Figure 3:
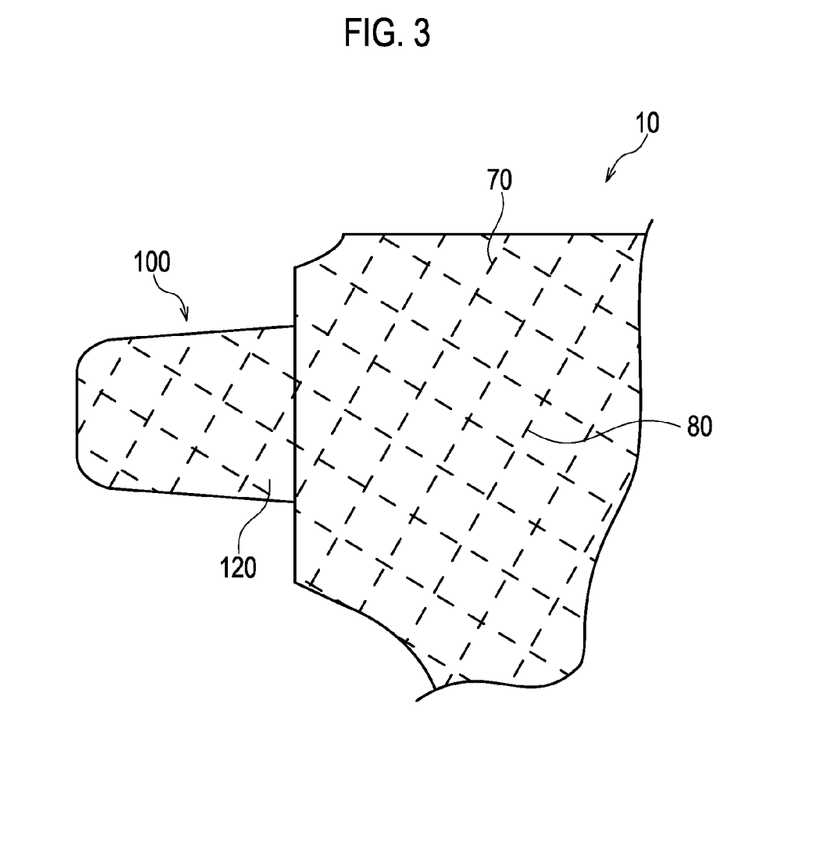
FIG. 3 is an enlarged view of the fastening tape 100 portion (a side of a backsheet 70) of the disposable diaper 10 according to the embodiment of the present invention.
Figure 4:
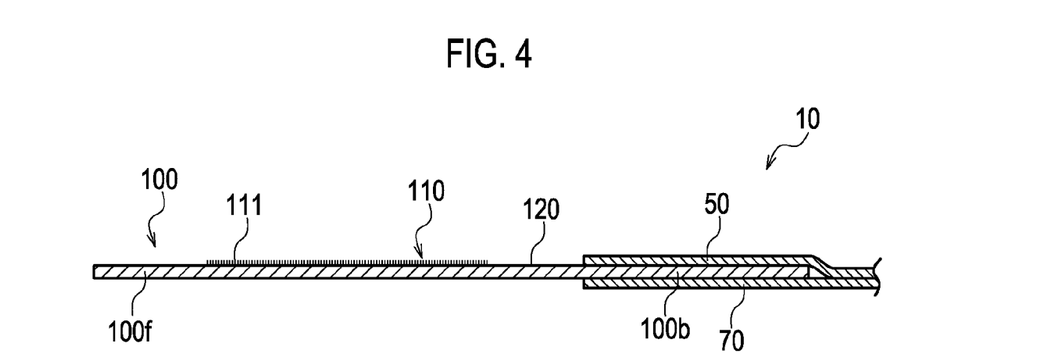
FIG. 4 is a cross-sectional view of the disposable diaper 10 along an F4-F4 line shown in FIG. 2.

Next, the shape of the fastening tape 100 is explained with reference to FIG. 2 through FIG. 4. FIG. 2 is an enlarged view of the fastening tape 100 portion (side flap 50 side) of the disposable diaper 10. FIG. 3 is an enlarged view of the fastening tape 100 portion (backsheet 70 side) of the disposable diaper 10. FIG. 4 is a cross-sectional view of the disposable diaper 10 along an F4-F4 line shown in FIG. 2.

As shown in FIG. 2 through FIG. 4, the fastening tape 100 is installed in the region of the side flaps 50 corresponding to the back waistline portion 40 (see FIG. 1). The fastening tape 100 has the hook sheet 110 provided with a plurality of engagement hooks 111 and a base sheet 120 made of nonwoven fabric. In addition, the base sheet 120 may be obtained by laminating a film on nonwoven fabric.

The hook sheet 110 is joined with the base sheet 120. The hook sheet 110 and the base sheet 120 are desired to be joined such that the stiffness of the fastening tape 100 does not become more than necessary. Specifically, the hook sheet 110 and the base sheet 120 are desired to be joined with a hot-melt adhesive applied intermittently in dot shape, line shape, or spiral shape. The hook sheet 110 and the base sheet 120 may also be joined with a heat seal, for example.

Furthermore, in order to reduce the stiffness of the hook sheet 110, various well-known methods, such as reducing the thickness of the base portion of the hook sheet 110, and increasing the gap of the base portion, can be used.

In the present embodiment, the size of the hook sheet 110 is larger than the size of a conventional standard hook sheet. Specifically, the width in the widthwise direction DW and the longitudinal direction DL is set between 20 and 40 mm, and between 30 and 50 mm, respectively. The width of the conventional standard hook sheet in the widthwise direction DW and the longitudinal direction DL is between 10 and 30 mm, and between 15 and 30 mm, respectively. Thus, because the size of the hook sheet 110 is large, even if the fastening tape 100 is made flexible by reducing the KES bending stiffness value of the fastening tape 100 described later and the height of the engagement hook 111 is low, the hook sheet 110 can be recognized easily.

Furthermore, the height of the engagement hook 111 is set between 60 and 200 μm. The hook sheet 110 provided with a height of the engagement hook 111 is well-known, and a hook sheet generally sold in the market is available. In addition, in the present embodiment, by applying heat and pressure to a commercial hook sheet passing between heating rollers having flat surfaces and by adjusting clearance between both rollers, a hook sheet having an engagement hook with a target height has been obtained.

The base sheet 120 is made of one or two or more sheets overlapping one another, specifically, nonwoven fabric, sheets obtained by laminating a film on nonwoven fabric, or the like. As the base sheet 120, it is possible to use a sheet obtained by laminating a thermoplastic film on various types of nonwoven fabric such as nonwoven fabric or spunbond (SB) which is manufactured using a manufacturing method such as spunbond, spunbond-meltblown-spunbond (SMS), and through air.

The base sheet 120, specifically, may have a configuration in which two or more sheets are overlapping one another. In such a case, the basis weight per one nonwoven fabric sheet is between 10 and 80 $g/m^2$, and preferably between 20 and 55 $g/m^2$. The total thickness of the base sheet 120 is between 150 μm and 550 μm, as described above, and preferably between 250 μm and 500 μm.

As described above, a plurality of sheets are used in the base sheet 120 such that the base sheet 120 is in the above-described range, so that it is possible to ensure appropriate flexibility as compared with the hook sheet 110, while ensuring strength or ease of treatment required as a factor for fixing the hook sheet 110 to the disposable diaper 10 and preventing a user from having a foreign body sensation as the impression of the thickness as compared with the hook sheet 110.

If the basis weight of the base sheet 120 exceeds 60 $g/m^2$, it is necessary to increase a thermally fusion bonding point, because of an increase in the volume of fibers of nonwoven fabric, in order to confound and fix the fibers each other constituting the nonwoven fabric, and the bending stiffness of the base sheet 120 becomes noticeable as compared with the bending stiffness of the hook sheet 110. Furthermore, if the thickness of the base sheet 120 exceeds 550 μm, since a user may have a foreign body sensation from a sense of thickness of the base sheet 120 (the impression of a cloth-like feel is changed to the impression of a plastic-like feel), it has an influence on a sense of unity between the hook sheet 110 and the base sheet 120.

Furthermore, if the basis weight of the base sheet 120 is lesser than 10 $g/m^2$, it is difficult for the base sheet 120 with the hook sheet 110 attached thereto to ensure sufficient strength. If the thickness of the base sheet 120 is lesser than 150 μm, it is difficult to perform attachment and detachment operations when the hook sheet 110 is fixed to the disposable diaper 10 and the hook sheet 110 is detached from the disposable diaper 10.

As described above, in relation to the base sheet 120, the plurality of sheets are allowed to overlap one another to reduce basis weight per one sheet (when the plurality of sheets overlap one another, it is more preferable to use nonwoven fabric having basis weight in the above-described range) as compared with the case of using nonwoven fabric of one sheet having heavy basis weight, and the plurality of sheets are divided into plural sheets of two or three and allowed to overlap one another and the total thickness is allowed to be equal to or less than 550 μm, so that it is possible to achieve the above-described target in a more balanced manner. In addition, the thickness of the nonwoven fabric has been measured, at 20 degrees as room temperature, using a thickness indicator (a thickness indicator manufactured by TESTER SANGYO Co., Ltd.) in which a measurement terminal has a circular shape (φ 5 mm) and a load is 1.23 N.

Furthermore, when the base sheet 120 is made of the plurality of sheets, the sheets may be joined to one another using various means. It is preferable that a hot-melt adhesive is applied in the form of a line (includes a spiral shape) or a dot to fix the sheets to one another, in terms of flexibility and productivity.

Specifically, when the base sheet 120 is made of nonwoven fabrics of two or more layers, it is preferable that the nonwoven fabrics are joined with one another in the form of a net-shaped pattern using 2 $g/m^2$ to 8 $g/m^2$ of an adhesive.

Furthermore, in the present embodiment, the fastening tape 100 has a shape such that as the fastening tape 100 extends from a proximal end 100b installed in the side flaps 50 towards a free end 100f positioned on the opposite side of the proximal end 100b, the width in the longitudinal direction DL of the absorbent main body 15 reduces.

The difference d between the width of the absorbent main body 15 along the longitudinal direction DL in the proximal end 100b and the width of the absorbent main body 15 along the longitudinal direction DL at the end of the hook sheet existent region SHS, towards the proximal end 100b, is 7.5 mm or less, preferably 5.0 mm or less, at one end in the longitudinal direction DL. Therefore, the existence of the proximal end 100b (joining part with the disposable diaper 10) can give a relatively small impression, and the sense of unity of the fastening tape 100 and the disposable diaper 10 can be raised.

Moreover, a corner of the free end 100f has a rounded shape. That is, the corner of the free end 100f is cut to be rounded and is not angular. Furthermore, the vicinity of the end of the side flap 50 on the proximal end 100b side is also cut to be rounded.

As shown in FIG. 3, embossed portions 80 are formed in the backsheet 70 of the disposable diaper 10. Furthermore, the embossed portions 80 having a similar pattern are formed in the fastening tape 100, specifically, in the base sheet 120 as well. That is, the outer surface of the base sheet 120, which is the surface at the opposite side of the surface in which the hook sheet 110 is provided, and the outer surface of the absorbent main body 15 are desired to have substantially the same pattern or the same color tone.

The work of "substantially the same color tone" means that one color and a comparison-target color have the same color phase or the neighbor color phase in the Ostwald hue circle.

Moreover, the nonwoven fabric of the backsheet 70 side and the nonwoven fabric of a non-skin contact surface side (clothes side) of the absorbent main body 15, that is, the surface of the backsheet 70, may have the same nonwoven fabric embossing pattern, or may use nonwoven fabric made of the same material (the type of fiber constituting the nonwoven fabric and the type of the nonwoven fabric are the same, more preferably, the basis weights thereof are approximately the same).

Figure 5:
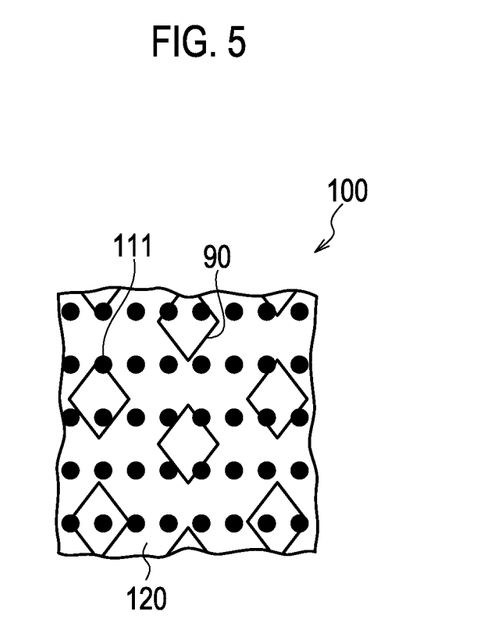
FIG. 5 is a partially enlarged plan view of the fastening tape 100 according to the embodiment of the present invention.

Furthermore, in the present embodiment, as illustrated in FIG. 5, the base sheet 120 has a hot embossed region 90 where hot embossing has been performed. Light transmittance of the hot embossed region 90 is different from light transmittance of a non-embossed region where hot embossing has not been performed.

In the present embodiment, the hot embossed region 90 is a rhomboidal shape (0.5 mm×1.0 mm). However, the shape of the hot embossed region 90 may not necessarily be a rhomboidal shape. For example, the hot embossed region 90 may have a rectangular or circular shape. The hot embossed region 90 is visible from the side of the hook sheet existent region SHS of the fastening tape 100. Furthermore, the size (diameter) of the upper end of the engagement hook 111 is smaller than the size of the hot embossed region 90.

The word of "visible" means that it is possible to see embossed patterns (designs) when an examinee who has a good eyesight (over 1.0) sees an object at a distance of about 30-50 cm in a brilliantly-lighted room (target: 500-750 lx) by neutral white (target of color temperature: 4600-5400 K).

Additionally, the color difference ΔE between the hook sheet existent region SHS on the inner side of the fastening tape 100 and the side flaps 50 adjacent to the fastening tape 100, specifically, the side flap region SSF where the side flaps 50 and the fastening tape 100 overlap, is 6.5 or more when the color difference of L* is ΔL*, the color difference of a* is Δa*, and the color difference of b* is Δb* according to the L*a*b* color coordinate system.

It is noted that ΔE can be calculated according to (Equation 1).

[Math. 1]

$$\Delta E = \sqrt{\Delta L^{*2} + \Delta a^{*2} + \Delta b^{*2}} \quad \text{(Equation 1)}$$

Furthermore, the light transmittance of the hook sheet 110 from the distal end side of the engagement hook 111 to the base sheet 120 side is preferably between 60% and 85%. The measurement of the light transmittance conforms to the standard of JIS-K7105 and was performed using a color-difference meter (a color-difference meter Z-300A using flicker photometry manufactured by Nippon Denshoku Industries Co., Ltd.). Specifically, a sample of 5 mm in width and 5 mm in length was sandwiched by a turbidimeter so as to evaluate a TT value, and the evaluated TT value was used as the total light transmittance (%) of the sample.

As shown in FIG. 4, the proximal end 100b of the fastening tape 100 is installed in the side flaps 50 and the backsheet 70. The fastening tape 100, and the side flaps 50 and the backsheet 70 are also desired to be joined with a hot-melt adhesive applied intermittently in dot shape, line shape, or spiral shape, as described above.

(3) BENDING STIFFNESS VALUE OF FASTENING TAPE

Next, a KES bending stiffness value of the fastening tape 100 is described. In addition, a specific measurement method of the KES bending stiffness value is described later.

In the present embodiment, in the fastening tape existent region SALL (see FIG. 2) provided with the fastening tape 100, the KES bending stiffness value per unit length in the longitudinal direction DL of the hook sheet existent region SHS provided with the hook sheet 110, and the KES bending stiffness value per unit length in the widthwise direction DW are equal to or less than 1.64 gf·cm²/cm.

(4) EXAMPLES

Next, examples of the present invention are described. Table 1 schematically illustrates configurations and test results of fastening tapes according to example 1 to example 6 and fastening tapes according to comparative example 1 to comparative example 3 (hereinafter, simply referred to as example and comparative example).

Furthermore, the overall dimension (fastening tape existent region SALL) in the widthwise direction DW of the fastening tape according to the examples and the comparative examples was 60 mm, the dimension of the hook sheet existent region SHS (including the free end 100f) was 25 mm, and the dimension of the adjacent region SB (region in which the hook sheet 110 does not exist) was 5 mm. Also, the dimension of the side flap region SSF in the widthwise direction DW was 20 mm.

[Table 1]

As illustrated in Table 1, using a plurality of samples, in which the type of nonwoven fabric used in the fastening tape, the basis weight of the base sheet 120, and the total thickness of the hook sheet 110 and the base sheet 120 are different from one another, a cloth-like feel and bending property (bending stiffness) of the fastening tape were tested.

Hereinafter, details of a measurement method and a test result of each test are described.

(4.1) Cloth-Like Feel

Using commercial "Moony Nenne-Jitate Size S" manufactured by Unicharm Corporation, and replacing a region including the fastening tape, the side flap portion having the fastening tape fixed thereto, and the backsheet portion, from a 20 mm position inside in the widthwise direction DW of a part to which the fastening tape and the side flaps have been fixed, test samples were prepared.

Furthermore, since the test was aimed at a person feeling the fastening tape as an "object (foreign body) having different hardness differently from a diaper body", screening was performed for persons subject to hearing to target persons having the above-described impression on a fastening tape of a disposable diaper usually used. Specifically, after the above screening was performed for mothers bringing up infants and toddlers of 2 months to 6 months filled with a feeling of dislike for a hard object or a sharp object due to a rise of motherhood, the following hearing of sensitive evaluation was performed for 30 mothers.

In the test, after the mothers freely touched the fastening tape of a sample, whether the mothers had cloth impression on a sense of feeling of the fastening tape was evaluated in the following five steps. Samples, in which the ratio of the number of persons having replied (1) or (2) had exceeded 60%, were marked by ○.

(1) Feeling the same as a sheet of a diaper body
(2) Feeling approximately the same as a sheet of a diaper body
(3) None of the above
(4) Feeling slightly different from a sheet of a diaper body
(5) Feeling different from a sheet of a diaper body In addition, the total thickness of the hook sheet 110 and the base sheet 120 was measured using the above-described thickness indicator (the thickness indicator manufactured by TESTER SANGYO Co., Ltd.).

(4.2) Bending Property

The bending properties of the fastening tape were measured by using the KES flexural property measuring machine manufactured by KATO TECH CO., LTD. Specifically, a B value (bending stiffness value) was measured.

Specifically, the details of the KES method are explained in "The Standardization and Analysis of Hand Evaluation" 2nd Edition (The Hand Evaluation and Standardization Committee, the Textile Machinery Society of Japan, Issued on Jul. 10, 1980). Thus, a measurement method of each mechanical property is described only for measurement conditions related to the present measurement.

The bending property was measured using KES-FB2 manufactured by KATO TECH Co., Ltd. by fixing each sample (samples obtained by cutting the hook sheet existent region SHS together with the base sheet 120) between chucks (the skin surface side (the inner side) of the fastening tape in the diaper is set as a downward direction), bending the sample to the front side up to maximum curvature +2.5 cm−1, bending the sample to the back side up to maximum curvature −2.5 cm−1, and returning the sample to the original position.

It should be noted that "MD bending" shown in Table 1 implies the bending in the longitudinal direction DL, and "CD bending" implies the bending in the widthwise direction DW.

(4.3) Hook Height

Based on the assumption that the engagement hook of the fastening tape was viewed when the disposable diaper was exchanged, the sample was viewed from a position separated by 30 cm to 50 cm, and whether the engagement hook gave "sharp impression or hard impression" was checked. Whether hearing existed in the impression of "feel" or "does not feel" was checked. Samples, in which the number of persons having the impression of "does not feel" has exceeded 70%, were marked by "OK". Table 2 illustrates the test result.

[Table 2]

In addition, the hook height of each sample was measured in the state in which no pressure was applied to it. Under the measurement environment in which temperature was 20±2° C. and relative humidity was 65±5%, a microscope (VHX-900 manufactured by KEYENCE Corporation) was used as a measuring instrument. First, an enlarged image obtained by enlarging the section of the sample was acquired and the sample having a well-known dimension was displayed on the image in layers. The scale of the microscope was adjusted according to the enlarged image, and the height and thickness of the sample were measured. This task was repeated 10 times, and an average value obtained for 10 times was used as an acquired value.

(4.4) Color Difference (L*a*b* Color Coordinate System)

The values of L*, a*, and b* of the hook sheet 110 (hook sheet existent region SHS), and the values of L*, a*, and b* of the base sheet 120 (adjacent region SB) adjacent to the hook sheet 110, and the side flaps 50 were measured.

Coordinates L, a, and b were measured by using a colorimeter (Minolta mode CR-300). Specifically, on a white standard plate, the base sheet 120 (a mounting surface of the hook sheet 110 is defined as an upper side) and the hook sheet 110 (a side of the engagement hook 111 is defined as an upper side) have been sequentially arranged. The size of the hook sheet 110 was smaller than the size of the base sheet 120, and the values of L*, a*, and b* in the position (adjacent region SB), in which only the base sheet 120 existed, were measured. Additionally, the values of L*, a*, and b* were measured at the position (hook sheet existent region SHS) where the hook sheet 110 and the base sheet 120 overlapped each other. In the same manner, on the white standard plate, a side of the backsheet 70 of the side flaps 50 was arranged downward, and the values of L*, a*, and b* in the side flaps 50 were measured.

Next, ΔE (see Equation 1) in each region, specifically, ΔE in various regions such as the hook sheet existent region SHS and the adjacent region SB, and the hook sheet existent region SHS and the side flaps 50, were calculated.

Table 3 illustrates measurement results of the example 1. Furthermore, Table 4 illustrates measurement results of example 2. As illustrated in Table 3 and Table 4, in the same example, a plurality of samples, in which the color of the base sheet 120 was changed, were tested. The hook height used in example 1 and example 2 was 100 μm.

[Table 3]
[Table 4]

In the example described in Table 3, the nonwoven fabric illustrated in Table 3 was used and the measurement was confirmed by using the colored nonwoven fabric. The hook sheet had a white base, and the hook height was 100 μm. In the example described in Table 4, the same nonwoven fabric as illustrated in Table 4 was used for the base sheet and the measurement was confirmed by using the colored nonwoven fabric. The hook sheet had a white base, and the hook height was 100 μm. It should be noted that the hook sheet can also be colored.

Furthermore, in Table 3 and Table 4, the region A corresponds to the hook sheet existent region SHS and the region B corresponds to the side flap region SSF.

In the "Ease of identifying the hook" test described in Table 3 and Table 4, the "Noticeability of the hook" was questioned, and the closest answer was selected from among the five answers given below. Samples, in which the ratio of the number of persons having replied (1) or (2) had exceeded 60%, were considered good (OK).

(1) Very smooth
(2) Slightly noticeable
(3) None of the above
(4) Not very noticeable
(5) Not noticeable at all
(5) Operation and Effect Depending on the disposable diaper 10, the KES bending stiffness value in the longitudinal direction DL of the hook sheet existent region SHS and the KES bending stiffness value in the widthwise direction DW is equal to or less than 1.64 gf·cm²/cm. Furthermore, the height of the engagement hook 111 is 60 to 200 μm. Additionally, the color difference ΔE between the hook sheet existent region SHS and the side flap region SSF of the side flaps 50 is 6.5 or more.

Thus, in the fastening tape 100 of the disposable diaper 10, it is possible to achieve texture and appearance the same as that of nonwoven fabric and the like, differently from plastic texture and appearance as with a conventional hook fastener. That is, it is possible to significantly reduce the uncomfortable feeling in texture and appearance of the fastening tape 100, and create a sense of unity with a worn article worn on a person and the like, such as a disposable diaper body.

Furthermore, in the fastening tape 100, whose difference from the disposable diaper 10 main body has been reduced, because the visual recognition of the provision of the fastening tape 100 is easy to make, the user does not get a feeling of insecurity regarding the original function of the fastening tape 100, which is to retain the disposable diaper 10 to the body. That is, according to the fastening tape 100, the impression of a relatively high quality disposable diaper 10 can be provided.

More specifically, by making a difference in color, as described above, to the fastening tape 100 that is the location of engagement, with respect to the adjacent location, it becomes easy to visually recognize the fastening tape 100. Particularly, it is necessary to offer the impression that a fastening tape 100 has been provided, when the diaper is laid against the body of the wearer, the fastening tape 100 is expanded towards the outside in the widthwise direction DW, and the inner side of the fastening tape 100 is visually recognized by the user. By offering such an impression to the user, the user can get a feeling of a good texture of the fastening tape 100 and can use the disposable diaper 10 without a feeling of insecurity.

Furthermore, in the present embodiments, the base sheet 120 is made of sheets (nonwoven fabrics) of two or more layers, and the basis weight per one sheet is between 10 and 60 g/m$^2$. Moreover, the total thickness of the nonwoven fabric is between 150 and 550 μm. The base sheet 120 is made of a plurality of sheets and has basis weight and thickness in the above-described range, so that it is possible to ensure the strength of the fastening tape 100 while reducing the bending stiffness value, and to achieve texture and appearance similar to nonwoven fabric and the like of the body of the disposable diaper 10.

In the present embodiments, the light transmittance of the hot embossed region 90 is different from the light transmittance of the non-embossed region where hot embossing has not been performed. Furthermore, the hot embossed region 90 is visible from the side of the hook sheet existent region SHS. Thus, the hot embossing pattern, which gives the impression as nonwoven fabric of the base sheet 120, is transparently visible, and the engagement hook 111 is formed to be smaller than the hot embossed region 90, resulting in the achievement of visual impression in which the engagement hook 111 is mixed in the hot embossed region 90. That is, it is difficult for a user to feel the existence of the engagement hook 111 having a sharp impression, and the foreign body sensation of the hook sheet 110 can be reduced further. Furthermore, by setting the light transmittance from the distal end side of the engagement hook 111 of the hook sheet 110 to the base sheet 120 side between 60% and 85%, the foreign body sensation of the hook sheet 110 can be reduced further.

In the present embodiments, the fastening tape 100 has a shape in which the width in the longitudinal direction DL is narrower from the proximal end 100*b* to the free end 100*f*, and the corner of the free end 100*f* has a rounded shape. Furthermore, the width of the fastening tape 100 is also narrower as compared with the conventional art. Therefore, it becomes easy to follow the shape of the inguinal portion around the legs of the wearer and the body type of the infants and toddlers in which their abdominal portion is often risen up, and it is possible to prevent the occurrence of discomfort when the free end 100*f* (a grip part) of the fastening tape 100 comes into contact with the skin of the infant and toddler, and a sense of security upon viewing can be achieved.

In the present embodiments, the outer surface of the base sheet 120, which is opposite to the surface on which the hook sheet 110 is provided, and the outer surface of the absorbent main body 15 have substantially the same pattern (the embossed portion 80). Furthermore, the outer surface of the base sheet 120 and the surface of the backsheet 70 may be made of nonwoven fabric having the same embossing pattern and fiber type.

Therefore, it can be recognized by the user of the disposable diaper 10 that the fastening tape 100 forms one part with the disposable diaper 10, and is not a separate region. In addition, since the outermost sheet (the backsheet 70) of the disposable diaper has a high contact frequency when a user (for example, a mother of an infant and toddler) puts the disposable diaper on an infant and toddler, a sheet having soft touch is used.

In the present embodiments, the base sheet 120 is made of nonwoven fabrics of two or more layers, and the nonwoven fabrics are joined with one another in the form of a net-shaped pattern using 2 g/m$^2$ to 8 g/m$^2$ of an adhesive. Thus, since the adhesive can be applied with smaller basis weight in a wider range as compared with applying in a line or plane shape and the nonwoven fabrics can be joined firmly in a partial manner, it is possible to achieve both joining strength and flexibility. In addition, at 2 g/m$^2$ or less, since the nonwoven fabrics are insufficiently joined to one another at the time of mounting of the fastening tape 100, delamination thereof may occur. At 8 g/m$^2$ or more, since the diameter of the adhesive (hot-melt) applied in the net-shaped pattern is increased, hardening due to joining may occur, which is not preferable.

(6) OTHER EMBODIMENTS

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

For example, in the aforementioned embodiment, the embossed portions 80 are formed in the outer surface of the base sheet 120, which is the surface at the opposite side of the surface in which the hook sheet 110 is provided, and the outer surface of the absorbent main body 15, because of which the outer surface of the base sheet 120 and the outer surface of the absorbent main body 15 have substantially the same pattern, however, such a process need not necessarily be performed.

It was explained in the aforementioned embodiment that the disposable diaper 10 can be used favorably for infants and toddlers, however, the applicability of the present invention is not limited to a disposable diaper for infants and toddlers, for example, the present invention can definitely be applied even to a disposable diaper for children and adults.

In the above-described embodiments, the open-type disposable diaper has been described as an example. However, the present invention can also be applied to a pant-type (reclosable) disposable diaper in which a front waistline portion and a back waistline portion are joined to be detachable. Specifically, the present invention can also be applied to a disposable diaper in which a fastening element corresponding to the fastening tape of the disposable diaper is provided to one of joining portion (a lateral portion) of the front waistline portion and the back waistline portion, and the lateral portion is attachable and detachable.

As described above, it is of course that the present invention includes various embodiments and the like not described here. Therefore, the technical range of the present invention is to be defined only by the inventive specific matter according to the adequate claims from the above description.

In addition, the entire content of Japanese Patent Application No. 2012-020378 (filed on Feb. 1, 2012) is incorporated in the present specification by reference.

INDUSTRIAL APPLICABILITY

It is possible to provide a disposable diaper that can offer an impression of having a sufficient engagement strength while significantly reducing the uncomfortable feeling in texture or appearance of a fastening tape.

The invention claimed is:

1. A disposable diaper, comprising:
a longitudinally elongated absorbent main body having a front waistline portion, a back waistline portion, and a crotch portion, and including a liquid-retentive absorber;
a side flap provided to a side edge in a widthwise direction of the absorbent main body; and
a fastening tape attached to the side flap, extending outwardly in the widthwise direction of the absorbent main body from one of the front waistline portion and the back waistline portion, and configured to be attached to the other one of the front waistline portion and the back waistline portion; wherein
the fastening tape has a base sheet, and a hook sheet provided with a plurality of engagement hooks,
a fastening tape existent region provided with the fastening tape includes a hook sheet existent region provided with the hook sheet,
a KES bending stiffness value of the hook sheet existent region per unit length in a longitudinal direction of the absorbent main body, and a KES bending stiffness value of the hook sheet existent region per unit length in the widthwise direction of the absorbent main body are equal to or less than 1.64 gf·cm$^2$/cm,
a height of the engagement hooks is between 60 and 200 μm, and
the color difference ΔE between the hook sheet existent region on an inner side of the fastening tape and the side flap adjacent to the fastening tape is 6.5 or more, when the color difference of L* is ΔL*, the color difference of a* is Δa*, and the color difference of b* is Δb* according to the L*a*b* color coordinate system wherein the base sheet has a plurality of hot embossed regions where hot embossing is performed and a non-embossed region where the hot embossing is not performed,
light transmittance of the hot embossed regions is different from light transmittance of the non-embossed region,
the hot embossed regions are visible from a side of the hook sheet existent region of the fastening tape, and
a diameter of an upper end of each of the engagement hooks is smaller than a maximum width of each of the hot embossed regions.

2. The disposable diaper according to claim 1, wherein the base sheet comprises two or more sheets, and
a basis weight of each sheet of the base sheet is 10 to 60 g/m$^2$.

3. The disposable diaper according to claim 1, wherein light transmittance of the hook sheet from a side of distal ends of the engagement hooks to a side of the base sheet is 60% to 85%.

4. The disposable diaper according to claim 1, wherein the fastening tape has
a proximal end attached to the side flap, and
a free end opposite to the proximal end,
a width of the fastening tape in the longitudinal direction of the absorbent main body decreases from the proximal end to the free end,
a corner of the free end has a rounded shape;
a width of the hook sheet in the longitudinal direction of the absorbent main body is between 30 mm and 50 mm, and
a length of the hook sheet in the widthwise direction of the absorbent main body is between 20 mm and 40 mm.

5. The disposable diaper according to claim 1, wherein
an outer surface of the base sheet, which is opposite to a surface on which the hook sheet is provided, and an outer surface of the absorbent main body have substantially the same pattern or color.

6. The disposable diaper according to claim 1, wherein
an outer surface of the base sheet, which is opposite to a surface on which the hook sheet is provided, and an outer surface of the absorbent main body are made of nonwoven fabric having the same embossing pattern and fiber type.

7. The disposable diaper according to claim 1, wherein
the base sheet comprises two or more layers of nonwoven fabrics; and
the layers of the nonwoven fabrics are joined to one another with an adhesive of 2 g/m$^2$ to 8 g/m$^2$ in a form of a net-shaped pattern.

8. The disposable diaper according to claim 1, wherein the hook sheet existent region includes
the entire hook sheet, and
only a portion of the base sheet which is overlapped by the entire hook sheet.

9. The disposable diaper according to claim 8, wherein, in the hook sheet existent region, the hook sheet extends over an entire width of the fastening tape in the longitudinal direction of the absorbent main body.

10. The disposable diaper according to claim 1, wherein
light transmittance of the hook sheet from a side of distal ends of the engagement hooks to a side of the base sheet is 60% to 85%,
the width of the hook sheet in the longitudinal direction is decreased outwardly in the widthwise direction of the absorbent main body, and is between 30 mm and 50 mm, and
a length of the hook sheet in the widthwise direction of the absorbent main body is between 20 mm and 40 mm.

* * * * *